US00PP23100P3

(12) United States Plant Patent
Harris

(10) Patent No.: US PP23,100 P3
(45) Date of Patent: Oct. 9, 2012

(54) AZALEA PLANT NAMED 'MNIHAR018'

(50) Latin Name: ***Rhododendron* sp.**
Varietal Denomination: MNIHAR018

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 164 days.

(21) Appl. No.: 12/807,038

(22) Filed: Aug. 25, 2010

(65) Prior Publication Data

US 2012/0054932 P1 Mar. 1, 2012

(51) Int. Cl.
*A01H 5/00* (2006.01)

(52) U.S. Cl. ..... Plt./240

(58) Field of Classification Search ..... Plt./240
See application file for complete search history.

*Primary Examiner* — June Hwu
(74) *Attorney, Agent, or Firm* — Jondle & Associates, P.C.

(57) ABSTRACT

A new and distinct variety of Azalea plant with spring and fall blooming, attractive, showy, single dark red flowers, easily propagated by semi-hardwood cuttings in late spring through summer and fall, moderate growth rate under normal fertilization and moisture conditions; broadly-rounded and freely-branching in habit, grows well in containers, thrives in shade or sun and is hardy in Zone 7, is disclosed.

3 Drawing Sheets

Genus and species: *Rhododendron* sp.
Variety denomination: 'MNIHAR018'.

BACKGROUND OF THE NEW PLANT

The present invention is a new and distinct variety of evergreen Azalea of the genus *Rhododendron*. This new Azalea, hereinafter referred to as 'MNIHAR018', was discovered in 2003 in Lawrenceville, Ga. 'MNIHAR018' originated from a planned cross hybridization in 1999 between the female azalea plant 'Jay Valentine' (unpatented) and the male azalea plant 'Conleb' (U.S. Plant Pat. No. 10,581) in a controlled environment in Lawrenceville, Ga. The present invention has a blooming period in spring and fall, a compact, dense and globose growth habit, and cold hardiness.

The new plant was first propagated via semi-hardwood cuttings in 2004 in Dearing, Ga. and has been asexually reproduced repeatedly by semi-hardwood cuttings in Dearing, Ga. for over 6 years. 'MNIHAR018' has been found to retain its distinctive characteristics through successive asexual propagations via semi-hardwood cuttings.

'MNIHAR018' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring through fall blooming;
2. Attractive, showy, dark red colored flowers;
3. Numerous single flowers;
4. Easily propagated by semi-hardwood cuttings in late spring through summer;
5. Moderate growth rate under normal fertilization and moisture conditions;
6. Compact, dense and globose growth habit;
7. Grows well in containers;

8. Thrives in shade or sun; and
9. Hardy in Zone 7.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of 5-year-old plants grown in filtered shade and full sun in 2009 in Dearing, Ga.

DETAILED BOTANICAL DESCRIPTION OF THE NEW PLANT

Figure 1:
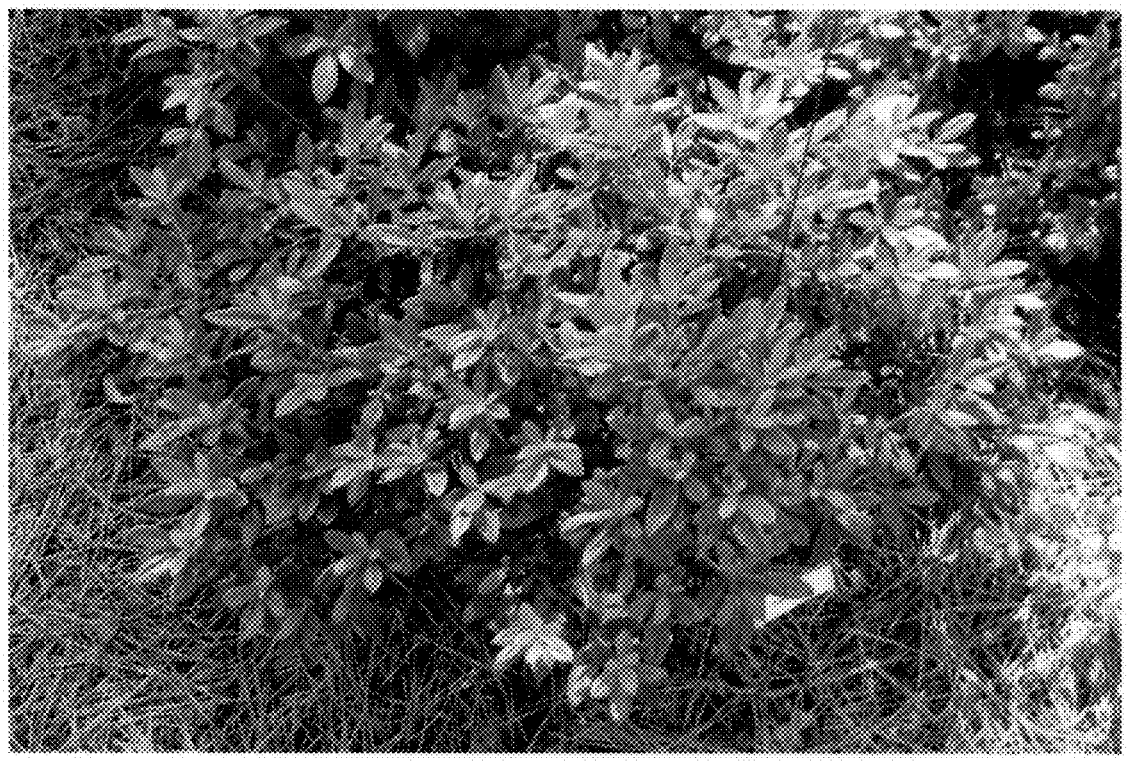
FIG. 1 shows mature foliage and growth habit of a five-year-old plant.
Figure 2:
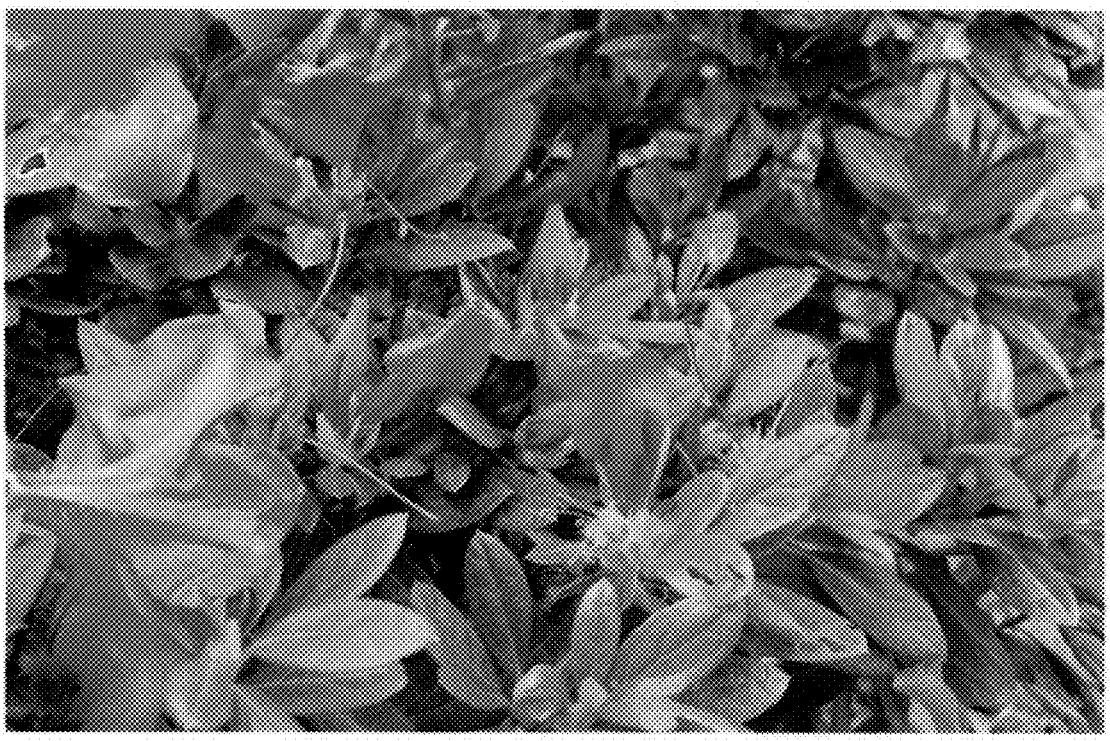
FIG. 2 is a close-up showing flower buds and mature foliage.
Figure 3:
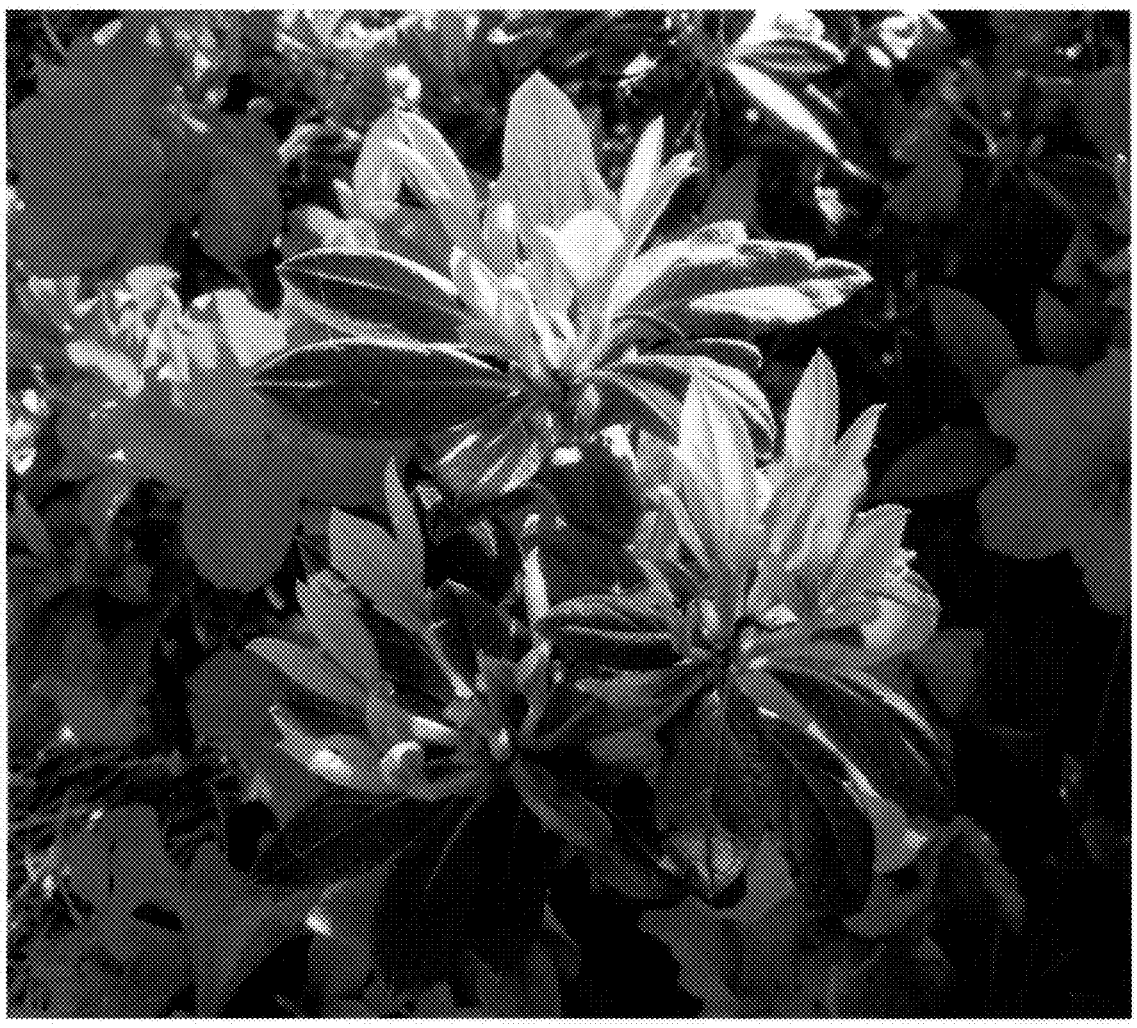
FIG. 3 is a close-up showing immature foliage.
Figure 4:
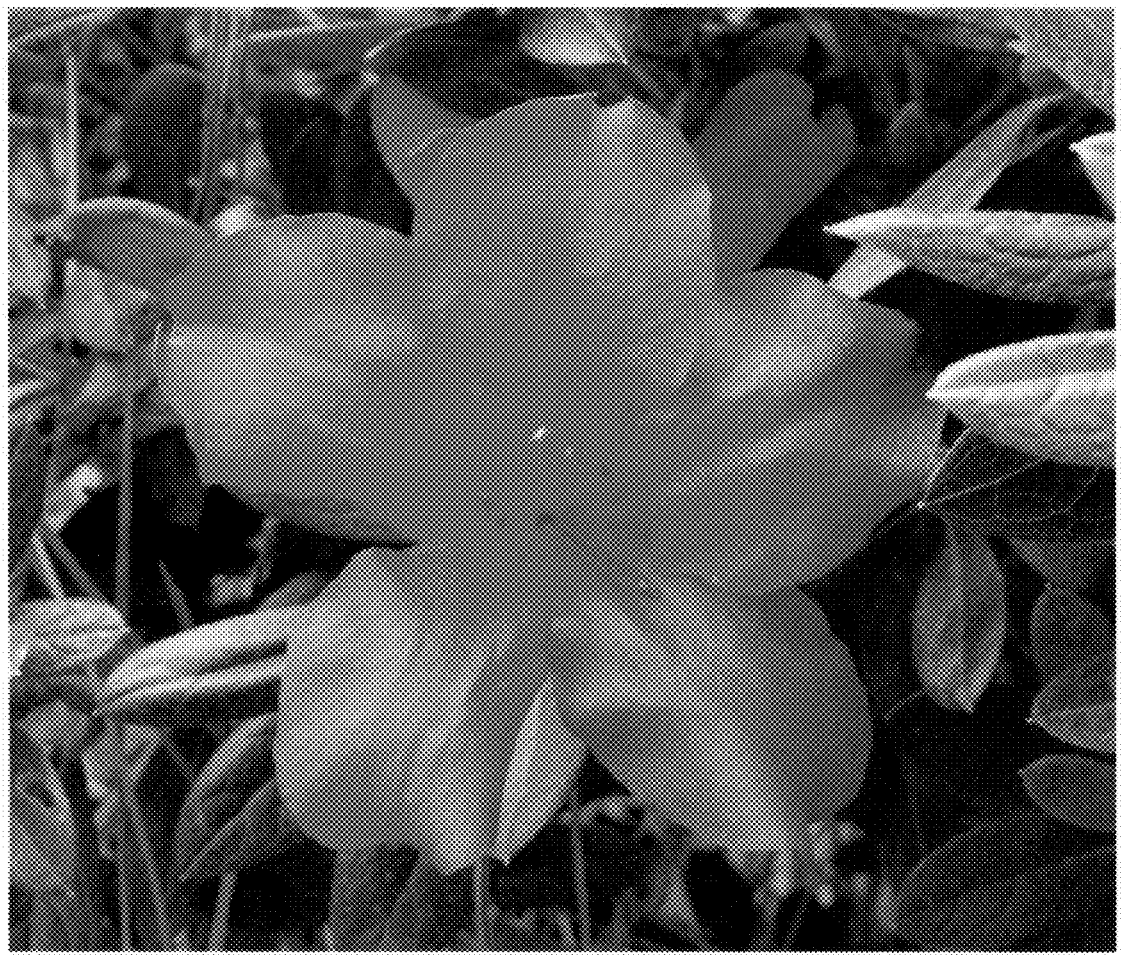
FIG. 4 is a close-up showing flower size, form, and color.

The following is a detailed description of the new variety of Azalea based on observations made of 5-year-old and 2-year-old plants grown in three-gallon and trade-gallon containers according to wholesale commercial production conditions, under full-sun and in an evaluation bed under semi-shade conditions in Dearing, Ga. in the spring, summer, and fall seasons of 2008, 2009, and 2010. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Commercial name*.—'MNIHAR018'.

Parentage:

*Female parent*.—The azalea plant 'Jay Valentine' (unpatented).

*Male parent*.—The azalea plant 'Conleb' (U.S. Plant Pat. No. 10,581).

Growth:

*Form*.—Compact, dense and globose.

*Texture*.—Medium.

*Height*.—76.2 cm to 91.44 cm.

*Width*.—91.44 cm to 121.92 cm.

*Growth habit*.—Freely-branching; dense and compact in nature.

*Growth rate*.—Moderate growth rate under normal fertilization and moisture conditions. In a period of 6 years from a rooted cutting the plant reaches a height of 42 cm and a spread of 78 cm. The growth rate is normally averages about 10.3 cm per year; the plant reaches a height of 76.2 cm to 91.44 cm at maturity while maintaining a dense habit due to the abundant branch development.

*Spring growth*.—The date of initial spring growth is April 1, followed by continuous growth through fall.

*Life cycle*.—Perennial and evergreen.

Leaves:

*Arrangement*.—Alternate, simple, pubescent, and evergreen.

*Shape*.—Oblanceolate to elliptic.

*Apex*.—Mucronate.

*Base*.—Attenuate.

*Margin*.—Entire.

*Length*.—3.8 cm.

*Width*.—1.3 cm.

*Venation pattern*.—Pinnate; the mid-veins and laterals are impressed on the upper surface and the prominent on the lower surface.

*Venation color*.—Upper surface: RHS 144B (yellow-green). Lower surface: RHS 147D (yellow-green).

*Immature leaf*.—Upper surface: Color: Matte, RHS 146B (yellow-green), RHS 144A (yellow-green), RHS 143A (green), and RHS 144C (yellow-green). Pubescence: Strigose and Scabrous uniformly covering the entire leaf surface. Pubescence color: RHS N155A (white) and RHS 164C (greyed-orange). Lower surface: Color: Matte, RHS 146C (yellow-green) and 144C (yellow-green). Pubescence: Scabrous with strigose. Pubescence color: RHS N155 (white).

*Mature leaf*.—Upper surface: Color: Semi-glossy, RHS 139A (green). Pubescence: Strigose and Scabrous. Pubescence color: RHS 166A (greyed-orange). Lower surface: Color: Semi-glossy, RHS 146A (yellow-green). Pubescence: Strigose. Pubescence color: RHS N167A (greyed-orange).

*Petiole*.—Length: 1.0 cm. Diameter: 0.2 cm by 0.1 cm. Pubescence: Strigose with some scabrous. Length: 0.05 cm to 0.1 cm. Color: Immature: RHS N155A (white). Mature: RHS 165D (greyed-orange). Color: Immature: RHS 147D (yellow-green). Mature: RHS 144B (yellow-green).

Stems:

*Form*.—Densely branched at terminal buds.

*Young stems* (1-*year-old and younger*).—Color: RHS 145C (yellow-green). Pubescence: Strigose. Pubescence color: RHS N155A (white) and RHS 164C (greyed-orange).

*Second-year stems*.—Color: RHS 197A (greyed-green) and RHS N199A (grey-brown). Pubescence: Strigose. Pubescence color: RHS 197C (greyed-green) in color. Length: 6.5 cm on average. Diameter: 0.35 cm. Pith: Solid and uniform. Internode length: Average 0.5 cm.

Flower buds:

*Arrangement and form*.—At terminals; borne in groups of two, three, or four, mostly three, sheathed by one to three modified leaf bracts. Length: average 1.3 cm. Width: 0.7 cm. Color: RHS 144B (yellow-green).

*Shape*.—Ovate.

*Apex*.—Acute.

*Base*.—Rounded.

*Length* (*at tight bud*).—1.0 cm.

*Diameter* (*at tight bud*).—0.5 cm.

*Bud scales*.—Length: 1.2 cm. Width: 0.7 cm.

*Color* (*of scales*).—Immature: RHS 145B (yellow-green). Mature: RHS 145A (yellow-green).

*Texture*.—Matte; Strigose pubescence. Pubescence color: RHS 164A (greyed-orange).

*Pedicel*.—Length: 0.7 cm. Diameter: 0.2 cm. Texture: Pubescent, hispid to pilose pubescence. Pubescence color: RHS 40D (red), RHS 164B (greyed-orange), and RHS N155A (white). Color: RHS N34A (orange-red).

*Calyx*.—Length: 0.5 cm. Diameter: 0.3 cm. Texture: Pubescent, hispid and wooly pubescence. Pubescence color: RHS N155A (white). Color: RHS N34A (orange-red) and RHS 144B (yellow-green).

Flowers:

*Type*.—Perfect, single flowers.

*Shape*.—Open funnel-shaped.

*Flowering habit and period*.—Borne on the current season's growth; four weeks beginning in early April in Dearing, Ga.; flowering resumes late July/early August and continues until frost which can be as late as November or December.

*Lastingness of flowers on the plant*.—4 to 6 days in the sun; 4 to 7 days in the shade; self-cleaning to slightly persistent.

*Fragrance*.—Absent.

*Diameter*.—6.4 cm.

*Depth*.—5 cm.

*Petals*.—Quantity per flower and arrangement: Five imbricate petals that are fused at the base and remain fused up to 2.3 cm from the base. Shape: Obovate. Apex: Rounded with some retuse. Base: Fused. Margin: Entire, undulate. Texture (both upper and lower surfaces): Glabrous upper surface, glabrous to pubescent at the base of lower surface. Pubescence: Hispid, RHS N155A (white). Average length: 4.2 cm. Average width: 2.3 cm. Color: Upper surfaces: RHS 46A (red). Lower surfaces: RHS 46B (red).

Reproductive parts:

*Pistil*.—Quantity and form: Single, non-petaloid. Length: 3 cm. Diameter: 0.1 cm. Stigma: Color: RHS 59A (red-purple). Diameter: 0.15 cm. Style color: RHS 46A (red). Ovary: Pubescent, pilose with 5 locules. Color: RHS N155A (white).

*Stamens*.—Number: 5 to 6 per flower; non-petaloid. Length: 1.7 cm. Color: RHS 47A (red). Filament: RHS 47A (red); 1.6 cm in length. Anther: Length: 0.2 cm. Width: 0.1 cm. Color: RHS 59A (red-purple) with areas of RHS 42B (red). Pollen: Moderate. Color: RHS 159D (orange-white).

Fruit:

*Maturity*.—The capsule matures in about 6 months in Dearing, Ga. and the fruit set is low and contains about 0 to 200 non-winged seeds.

*Length*.—0.6 cm.

*Width*.—0.5 cm.

*Color*.—RHS 147B (yellow-green).

CULTURE

'MNIHAR018' grows well in a wide range of conditions and tolerates sun to shade. 'MNIHAR018' prefers moist, well-drained soil that is rich in organic matter and responds well to mulching and medium applications of fertilizer. 'MNIHAR018' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, the 'MNIHAR018' is compared to parental varieties 'Jay Valentine' (unpatented) and 'Conleb' (U.S. Plant Pat. No. 10,581) and lists the differences between the varieties.

TABLE 1

| Characteristic | 'MNIHAR018' | 'Jay Valentine' | 'Conleb' |
|---|---|---|---|
| Plant Height (Mature) | 91.44 cm to 106.68 cm | 121.92 cm | 121.92 cm to 152.4 cm |
| Flower Diameter | 6.4 cm | 6.25 cm to 7.62 cm | 6.5 cm |
| Flower Form | Single | Single | Single to semi-double |
| Flower Color | Dark Red | Deep Red | Red |
| Bloom Period | April and late July until frost | April | April and late July until frost |
| Hardy Zone | 7 | 7 | 7 |
| Stamen Number | 5 to 6 | 5 | 0 to 9 |
| Stamen Type | Non-petaloid | Petaloid | Petaloid and Non-petaloid |

When 'MNIHAR018' is compared to the commercial variety 'Roblen' (U.S. Plant Pat. No. 16,248), 'MNIHAR018' has a compact, dense and globose growth habit with a height of 42 cm and a spread of 78 cm in 6 years, while 'Roblen' has a height of 91.44 cm and a spread of 60.96 cm in six years. Additionally, 'MNIHAR018' produces dark red flowers, while 'Roblen' has bright red flowers.

I claim:

1. A new variety of Azalea plant named 'MNIHAR018' as herein shown and described.

* * * * *